United States Patent [19]

Tarayre et al.

[11] 4,225,610
[45] Sep. 30, 1980

[54] IMMUNOACTIVATORS DERIVED FROM AMINO THIAZOLES

[75] Inventors: Jean-Pierre Tarayre, Valdurenque; Henri Cousse, Chemin de Lastino; Gilbert Mouzin; Henri Lauressergues, both of Castres, Tarn, all of France; Silvano Casadio, Milan, Italy

[73] Assignee: Pierre Fabre, S.A., France

[21] Appl. No.: 952,739

[22] Filed: Oct. 19, 1978

[30] Foreign Application Priority Data

Oct. 19, 1977 [FR] France ................................ 77 31687

[51] Int. Cl.² .......................................... C07D 277/20
[52] U.S. Cl. .................................... 424/270; 548/195
[58] Field of Search .................... 260/306.8; 424/270; 548/195

[56] References Cited

U.S. PATENT DOCUMENTS 4,134,984 1/1979 Crossley ........................ 260/306.8 R Primary Examiner—Nicholas S. Rizzo
Attorney, Agent, or Firm—Gordon W. Hueschen

[57] ABSTRACT

The present invention concerns new derivatives of 4-phenyl 2-amino thiazole of the formula

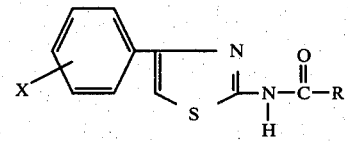

in which
X represents a hydrogen atom, a halogen, a lower alkyl or an alkoxy,
R is a hydrogen, a haloalkoxy, a substituted or unsubstituted aryl, a pyridyl, an aryloxy or a carboxy alkyl, having immunomodulating properties, useful in the treatment of rheumatoid arthritis and other ailments requiring immunotherapy.

13 Claims, No Drawings

IMMUNOACTIVATORS DERIVED FROM AMINO THIAZOLES

The present invention, developed at the Pierre Fabre Research Center, concerns new chemical derivatives, their method of preparation, and their use in therapy. They have immuno-modulating properties and are useful, in particular, in the treatment of rheumatoid polyarthritis and in immunotherapy generally.

The invention also relates to pharmaceutical compositions containing these active principles.

The chemical compounds which form the object of the invention have the general formula

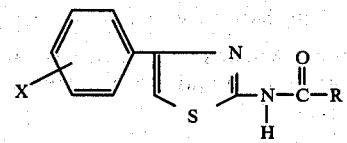

in which X represents a hydrogen atom, a halogen, a lower alkyl, or an alkoxy,

R represents a halo-alkoxy group, for instance —O—C—Cl$_3$, —O—CH$_2$—CCl$_3$; O—CH$_2$—CH$_2$—Br, etc., a substituted or nonsubstituted aryl radical, a pyridyl radical, an aryloxy radical or a carboxyalkyl radical.

These new chemical compounds are obtained in accordance with the following reaction:

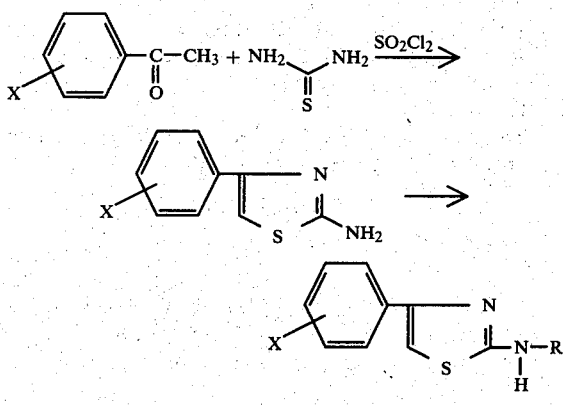

The following chemical compounds and their method of preparation are described by way of illustration and not of limitation. For the sake of convenience they are designated by a code number in order to facilitate the presentation of the text and the setting forth of the results of the experiments to which they have been subjected.

EXAMPLE 1

4-phenyl 2-amino thiazole (F 1653)

Carefully mix 360 g (3 mols) of acetophenone and 455 g (6 mols) of thiourea; then add 264 ml (3.3 mols) of sulfuryl chloride in small fractions. The reaction is exothermic and the sulfuryl chloride is added over the course of two hours.

The reaction medium liquefies and then sets; at this time bring to 105° C. for 3 hours.

Allow it to return to room temperature; wash with acetone and then filter.

The crystals obtained are recrystallized from 3 liters of boiling water.

Recover the hydrochloride of the amine, which is then treated with an ammonia solution until obtaining a pH of 12.

412 g of base are recovered upon filtration and drying.

Yield 78%.

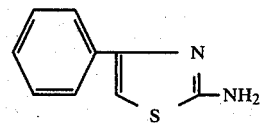

Empirical formula: C$_9$H$_8$N$_2$S
Molecular weight: 176.24
White crystals.
Melting point: 150° C.
Thin-layer chromatography
support: silica gel 60 F 254 Merck
solvent: acetic acid - dioxane - benzene 2-8-90
development: UV and iodine
Rf: 0.34
Solubility: insoluble in water, 1% soluble in ethanol, and 20% soluble in dimethyl pyrrolidone.

EXAMPLE 2

4-Parachloro-phenyl 2-amino thiazole (F 1654)

In a manner similar to that described in Example 1 but using parachloroacetophenone, there is obtained the product of the formula:

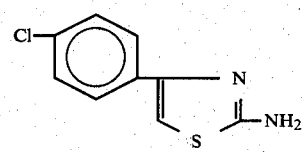

Epirical formula: C$_9$H$_7$ClN$_2$S
Molecular weight: 210.67
Crystals: yellow
Melting point: 166°–167° C.
Thin-layer chromatography:
support: silica gel 60 F 254 Merck
solvent: acetic acid - dioxane - benzene 2-8-90
development: UV and iodine
Rf: 0.3
Solubility: insoluble in water, 15% soluble in ethanol.

EXAMPLE 3

4-Paramethyl-phenyl 2-amino thiazole

In a manner similar to that described in Example 1 but using paramethylacetophenone, there is obtained the product of the formula:

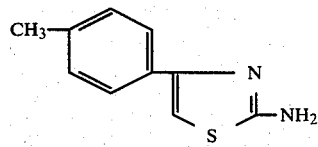

EXAMPLE 4

4-Paramethoxy-phenyl 2-amino thiazole

In a manner similar to that described in Example 1 but using paramethoxyacetophenone there is obtained the product of the formula:

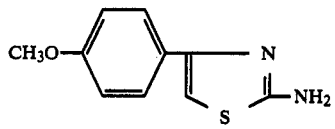

EXAMPLE 5

4-phenyl lauryl 2-amino thiazole (F 1655)

To a suspension of 35.2 g (0.2 mol) of 4-phenyl-2-amino thiazole and 20 g (about 0.2 mol) of triethylamine in 500 ml of chloroform, add, with vigorous agitation, 55.6 g of lauryl chloride.

Maintain the agitation for four hours at room temperature. Treat the organic phase with a solution of hydrochloric acid (normal) then wash with water and dry over sodium sulfate.

Filter and evaporate to dryness; upon recrystallization from ethanol there are recovered 38.5 g (yield 53%) of a product of the formula:

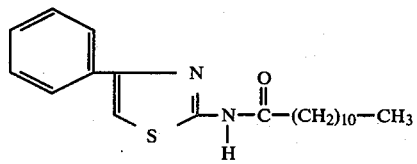

Empirical formula: $C_{21}H_{30}N_2OS$
Molecular weight: 358.55
Crystals: white
Melting point: 138°–139° C.
Thin-layer chromarography:
support: silica gel 60 F 254 Merck
solvent: acetic acid - dioxane - benzene 2-8-90
development: UV and iodine
Rf.: 0.64
Solubility: insoluble in water, 25% soluble in DMA and in methyl pyrrolidone.

EXAMPLE 6

4-phenyl 2-stearamido thiazole (F 1656)

In a manner similar to that described in Example 5 but using stearyl chloride, there is obtained the product of the formula:

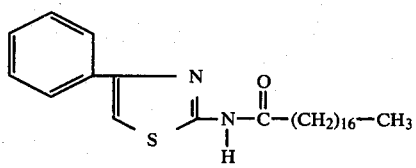

Empirical formula: $C_{27}H_{42}N_2OS$
Molecular weight: 442.71
Crystals: yellow
Melting point: 137° C.

Thin-layer chromatography:
support: silica gel 60 F 254 Merck
solvent: acetic acid - dioxane - benzene 02-08-90
development: UV and iodine
Rf: 0.70
Solubility: insoluble in water, 20% soluble in DMA; 20% soluble in methyl pyrrolidone.

Other long-chain alkylamides wherein the alkyl chain contains 8–28 carbon atoms, inclusive, e.g., octylamido, decylamido, eicosylamido, and octacosylamido, and the like, are prepared in the manner of Examples 5 and 6. These compounds have the same activity and uses as the other compounds of this invention and a favorable toxicity and therapeutic ratio.

EXAMPLE 7

N(4-phenyl 2-thiazolyl) nicotinamide (F 1684)

In a manner similar to that described in Example 5, but using nicotinyl chloride, there is obtained a product of the formula:

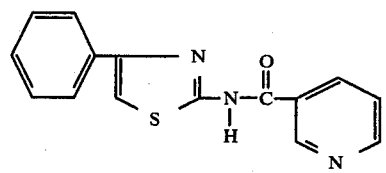

Empirical formula: $C_{15}H_{11}N_3OS$
Molecular weight: 281.26
Crystals: yellow
Melting point: 224°–225° C.
Thin-layer chromatograhy:
support: silica gel 60 F 254 Merck
solvent: acetic acid - dioxane - benzene -02-08-90
development: UV and iodine
Rf.: 0.32
Solubility: insoluble in water, 5% soluble in methyl pyrrolidone and 5% soluble in DMA.

EXAMPLE 8

N(4-parachloro phenyl 2-thiazolyl) nicotinamide (F 1685)

In a manner similar to that described in Example 5 but using nicotinoyl chloride and 4-parachlorophenyl 2-amino thiazole, there is obtained a product of the formula:

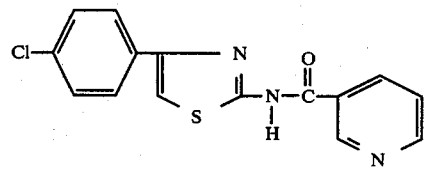

Empiricial formula: $C_{15}H_{10}ClN_3OS$
Molecular weight: 315.78
Crystals: yellow
Melting point: 263°–264° C.
Thin-layer chromatography:
support: silica gel 60 F 254 Merck
solvent: acetic acid - dioxane - benzene 02-08-90
development: UV and iodine
Rf: 0.48

Solubility: insoluble in water, 20% soluble in DMA, 20% soluble in methyl pyrrolidone.

EXAMPLE 9

N(4-phenyl 2-thiazolyl) succinamic acid (F 1657)

35.2 g of 4-phenyl 2-amino thiazole are dissolved in 350 ml of boiling 1-2 dichloroethane. To this solution add 20 g of succinic anhydride. The amide formed crystallizes; keep under reflux for five hours and filter. By recrystallization from alcohol there are recovered 39 g (70%) of the product of the formula

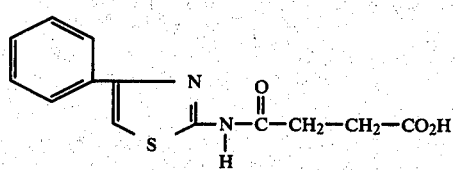

Empirical formula: $C_{13}H_{12}N_2O_3S$
Molecular weight: 276.31
Crystals: white
Melting point: 224° to 225° C.
Thin-layer chromatography:
support: silica gel 60 F 254 Merck
solvent: acetic acid - dioxane - benzene 02-08-90
development: UV and iodine
Rf: 0.34
Solubility: insoluble in water, 20% soluble in DMA, and 25% soluble in methyl pyrrolidone.

EXAMPLE 10

N(4-parachlorophenyl 2-thiazolyl) succinamic acid (F 1683)

In a manner similar to that described in Example 9 but using 4-parachlorophenyl 2-amino thiazole, there is obtained the product of the formula:

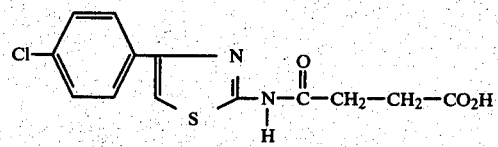

Empirical formula: $C_{13}H_{11}ClN_2O_3S$
Molecular weight: 310.76
Crystals: white
Melting point: 260°–261° C.
Thin-layer chromatography:
support: silica gel 60 F 254 Merck
solvent: acetic acid - dioxane - benzene 02-08-90
development: UV and iodine
Rf: 0.23
Solubility: insoluble in water, 20% in DMA and 20% soluble in methyl pyrrolidone.

EXAMPLE 11

4-phenyl-2-(2'-2'-2'-trichloro ethoxy carboxamido) thiazole (F 1686)

To a solution of 35.2 g of 4-phenyl 2-amino thiazole in 150 ml of acetone add 20 g of bicarbonate.

Then, with vigorous agitation, slowly add 42 g of α,α,α-trichloroethyl chloroformate.

Continue the agitation for one night at room temperature. Filter and evaporate to dryness; the residual mass is recrystallized from a 50/50 mixture of alcohol and water. There are recovered 32 g (55%) of product of the formula:

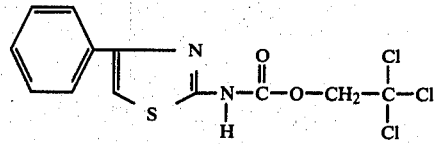

Empirical formula: $C_{12}H_9Cl_3N_2O_2S$
Molecular weight: 351.64
Crystals: white
Melting point: 126° C.
Thin-layer chromatography:
support: silica gel 60 F 254 Merck
solvent: acetic acid - dioxane - benzene 02-08-90
development: UV and iodine
Rf: 0.61
Solubility: insoluble in water, 3% soluble in ethanol, 25% soluble in DMA and 20% soluble in methyl pyrrolidone.

EXAMPLE 12

4-phenyl 2-phenoxy carbamoyl thiazole (F 1659)

In a manner similar to that described in Example 11 but using phenyl chloroformate there is obtained a product of the formula:

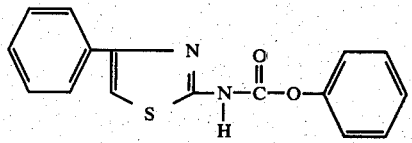

Empirical formula: $C_{16}H_{12}N_2O_2S$
Molecular weight: 296.35
Crystals: white
Melting point: 220° C.
Thin-layer chromatography:
support: silica gel 60 F 254 Merck
solvent: acetic acid - dioxane - benzene 02-08-90
development: UV and iodine
Rf: 0.73
Solubility: insoluble in water, 4% soluble in DMA and 3% soluble in methyl pyrrolidone.

EXAMPLE 13

4-phenyl 2-(ethoxy carboxamido) thiazole (F 1658)

In a manner similar to that described in Example 11 but using ethyl chloroformate, there is obtained a product of the formula:

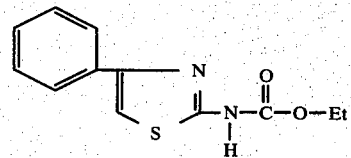

Empirical formula: $C_{12}H_{12}N_2O_2S$
Molecular weight: 248.30
Crystals: yellow
Melting point: 149°–150° C.

Thin-layer chromatography:
support: silica gel F 60 254 Merck
solvent: acetic acid - dioxane - benzene 02-08-90
development: UV and iodine
Rf: 0.63
Solubility: insoluble in water, 25% soluble in DMA and 25% soluble in methyl pyrrolidone.

EXAMPLE 14

4-parachlorophenyl 2-(2'-2'-2'-trichloro ethoxycarbamido) thiazole (F 1660)

In a manner similar to that described in Example 11 but using 4-parachlorophenyl 2-amino thiazole and α,α,α-trichloroethyl chloroformate, there is obtained a product of the formula:

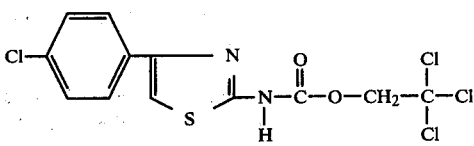

Empirical formula: $C_{12}H_{18}Cl_4N_2O_2S$
Molecular weight: 386.08
Crystals: beige
Melting point: 200° C.
Thin-layer chromatography:
support: silica gel 60 F 254 Merck
solvent: acetic acid - dioxane - benzene 02-08-90
development: UV and iodine
Rf: 0.75
Solubility: insoluble in water, 20% soluble in DMA and in methyl pyrrolidone.

Other haloalkoxy compounds, e.g., the corresponding β-bromoethoxycarbamido and β,β-dibromoethoxycarbamido compounds, are prepared in the same way as in Example 14 starting with the corresponding chloroformate.

EXAMPLE 15

4-parachlorophenyl 2-phenoxycarbamoyl thiazole (F 1687)

In a manner similar to that described in Example 11 but using 4-parachlorophenyl 2-amino thiazole and phenyl chloroformate there is obtained the product of the formula:

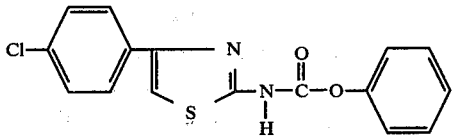

Empirical formula: $C_{16}H_{13}ClN_2O_2S$
Molecular weight: 330.79
Crystals: white
Melting point: 249°-250° C.
Thin-layer chromatography:
support: silica gel 60 F 254 Merck
solvent: acetic acid - dioxane - benzene 02-08-90
development: UV and iodine
Rf: 0.71;
Solubility: insoluble in water, 5% soluble in DMA, and 5% soluble in methyl pyrrolidone.

Other haloalkoxy compounds, e.g., the corresponding β-bromoethoxycarbamido and β,β-dibromoethoxycarbamido compounds, are prepared in the same way as in Example 15 starting with the corresponding chloroformate. Likewise, the chlorine atom may be replaced by another halogen atom, e.g., flourine or bromine, and any halogen in the phenyl ring may be in either the ortho, meta, or para position, or in any combination thereof, depending only upon the particular selected starting material employed.

PHARMACOLOGY

I—Showing of immunomodulating activity (1) Technique: cutaneous delayed hypersensitivity reaction to tuberculin in albino guinea pigs. (Method of G. L. FLOERSHEIM—Helv. Physiol. Acta 22, 92, 1964, as modified)

(a) Sensitization

Killed Mycobacterium tuberculosis are used. A well homogenized suspension of 80 mg of Mycobacterium tuberculosis (previously passed through a mortar) in 10 ml of Freund's incomplete adjuvant+10 ml of 0.2 M phosphate buffer (pH about 7).

0.5 ml of this suspension are injected intravenously into the thigh of the guinea pig.

(b) Challenge

At different times after the sensitization, the purified antigen (PPD) is injected intradermally in an amount of 5 μg, by injection into the shaved flanks of the guinea pig.

One thus forms four papules per flank. 24 hours later, erythemas of elliptical shape are observed at the place of the injections. Two perpendicular diameters of each papule are measured in order to calculate the area thereof.

(c) Treatment by the products to be studied

The products are administered around the period of the challenge injection in accordance with the following procedure: The products are administered subcutaneously, dissolved in dimethyl sulfoxide (DMSO) in 3 portions: 24 hours and 2 hours before the injections of PPD, with the final administration given two hours thereafter.

(2) Results

Table 1 sets forth the results obtained with F 1686 and levamisole (L-tetramisole).

In the control animals, the cutaneous delayed hypersensitivity response to the PPD is greater the longer the time between the sensitization and the challenge. (Results not reported here show that after 6 weeks the response remains constant).

Administered close to the period of challenge, F 1686 and levamisole to a definitely lesser degree stimulate the response when the response is of low intensity in the controls (that is to say when the time between the sensitization and the challenge is two to three weeks), while they do not modify it significantly any longer after a certain intensity has been reached (after 5 and 6 weeks).

(3) Conclusions

These results illustrate the concept of immunomodulating agents; these products, under certain conditions of administration (in this case near the period of challenge), restore the immunity response (essentially the cellular immunity) when the latter is depressed. When the response is normal, they no longer have any significant action. Within the scope of our experiments, F 1686 does not stimulate the reaction to the PPD except when the guinea pigs are in a state of hypoimmunization.

II—Action on Pleurisy of Delayed Hypersensitivity to Bordetella pertussis in Rats After Chronic Treatment (1) Technique based on:

DIEPPE P. A., WILLOUGHBY D. A., HUSKISSON E. C., ARRIGONI-MARTELLI Agents and actions 6, 618, 1976

TARAYRE J. P., DELHON A., H LAURESSERGUES, A. Inst. Pharmacodyn. 228, 162, 1977.

(a) Sensitization

Male rats weighing 280-320 g are used. The suspension of Bordetella pertussis used is the pertussis vaccine of the Pasteur Institute ($5 \times 10^9$ killed bacilli per ml). The Bordetella pertussis suspension is mixed (V/V: 50/50) with Freund's complete adjuvant. 0.2 ml of this mixture is injected intramuscularly into each thigh of the rat.

(b) Challenge 6 days later, 0.1 ml of the Bordetella pertussis suspension is injected into the pleural cavity. 48 hours later, the pleural exudate formed is removed and measured. The total number of leukocytes and the number of mononuclears and polynuclears of the exudate are determined.

(c) Treatment

The products studied were administered chronically in accordance with two procedures:

Procedure 1: The treatment commences on the day of the sensitization and continues at the rate of one administration per day until the challenge injection. On the day of the latter the compounds are given twice: one administration before and one after the intrapleural injection of the antigen. The animals are treated a last time 24 hours later.

Procedure 2: The treatment commences three weeks before the sensitization. During these three weeks, the products are given at the rate of 5 times per week. The treatment is then continued as indicated above in Procedure 1.

(2) Results

The results are set forth in Table 2.

Administered orally in chronic treatment in a dose of 5 mg/kg/administration, F 1686 and F 1654 reduce the delayed hypersensitivity pleural inflammation. Their action is superior to that of levamisole and appears during the course of the two treatment procedures employed. The effect of the products relates to the volume of the exudate and also to the cellular phenomena of the reaction.

TOXICOLOGY (I) Acute Toxicity (a) Technique

The acute toxicity after a single administration of the products per os was studied in mice.

The compounds were placed in suspension in a mixture of Tween 80 TM and distilled water. The mortality was noted at the end of 7 days. In the case of the products showing mortality in 1 g/kg or lower doses, the $LD_{50}$ (dose resulting in 50% mortality) was determined by the technique of MILLER C. and TAINTER M. L., Proc. Soc. Exper. Biol. Med. 57, 261, 1944.

(b) Results: The results are set forth in Table 3.

(II) Chronic Toxicity

Administered per os for two months to rats, F 1686 does not result in any toxic phenomenon up to a dose of 30 mg/kg/day.

TABLE 1

Action of F 1686 and of leyamisole, administered around the period of challenge, on the cutaneous reaction of guinea pigs to the PPD.

| Period between the sensitization and the challange | Lots | Parameters | Area of the erythema at + 24 hours (in mm$^2$) |
|---|---|---|---|
| 2 weeks | Controls DMSC 1 mg/kg (x 3) | mean ± standard error | 3,4 ± 1,8 (3,24) |
| | F 1686 5 mg/kg (x 3) | mean ± standard error Significant action | 29,8 ± 1,8 (3,24) + 776% P <0,01 |
| | Levamisole 5 mg/kg (x 3) | " | 6,8 ± 4,9 (2,16) + 100% P <0,05 |
| 3 weeks | Controls | | 54,4 ± 11,1 (6,47) |
| | F 1686 5 mg/kg (x 3) | | 98,9 ± 8,6 (7,55) + 82% - P <0,01 |
| | Levamisole 5 mg/kg (x 3) | | 72,4 ± 7,8 (7,56) + 33% - P >0,05 |
| 5 weeks | Controls | | 101,3 ± 9,2 (3,20) |
| | F 1686 5 mg/kg (x 3) | | 99,3 ± 6,9 (3,20) − 2% P >0,05 |
| | Levamisole 5 mg/kg (x 3) | | 83,7 ± 5,0 (3,24) − 17% P >0,05 |
| 6 weeks | Controls | | 144,3 ± 7,7 (5,37) |
| | F 1686 5 mg/kg (x 3) | | 140,1 ± 8,1 (8,46) − 3% P >0.05 |

*Within perenthesis, in order (number of guinea pigs, number of papules)

TABLE 2

Delayed Hypersensitivity Pleurisy to Bordetella pertussis in Rats

| Products | Treatment procedure | Doses mg/kg | Manner of administration | Action on the volume of exudate | Action on the total number of leukocytes | Action on the number of mononuclears | Action on the number of polynuclears |
|---|---|---|---|---|---|---|---|
| F 1686 | 1 | 5 | p.o. | −35% (35) p < 0,05 | −19% p < 0,05 | −21% p < 0,05 | −16% p > 0,05 |
| Levamisole | 1 | 5 | p.o. | −22% (36) p > 0,05 | −10% p > 0,05 | −11% p > 0,05 | −9 p > 0,05 |
| F 1686 | 2 | 5 | p.o. | −50% (29) | −22% | −29% | −6% |

TABLE 2-continued

| | | | | Delayed Hypersensitivity Pleurisy to Bordetella pertussis in Rats | | | |
|---|---|---|---|---|---|---|---|
| Products | Treatment procedure | Doses mg/kg | Manner of administration | Action on the volume of exudate | Action on the total number of leukocytes | Action on the number of mononuclears | Action on the number of polynuclears |
| | 2 | 5 | p.o. | $p < 0,05$ $-42\% (21)$ $p < 0,01$ | $p < 0,05$ | $p < 0,01$ | $p > 0,05$ |
| Levamisole | 2 | 5 | p.o. | $-23 (29)$ $p < 0,05$ | $-13\%$ $p < 0,01$ | $-17\%$ $p < 0,01$ | $-7\%$ $p > 0,05$ |
| F 1654 | 2 | 5 | p.o. | $-41\% (22)$ $p < 0,01$ | | | |

*Treatment procedure 1: treatment commencing on the day of the sensitization
Treatment procedure 2: treatment commencing 3 weeks after the sensitization.

TABLE

Acute Toxicity per os after a Single Administration of the Products

| Products | Dose in mg/kg | No. of mice per lot | Mortality at the end of 7 days | $LD_{50}$ in mg/kg |
|---|---|---|---|---|
| F 1653 | 100 | 5 | 0 | 140 |
| | 200 | 5 | 5 | |
| F 1654 | 200 | 5 | 0 | 300 |
| | 300 | 5 | 3 | |
| | 500 | 5 | 5 | |
| F 1655 | 1000 | 5 | 0 | >1000 |
| F 1656 | 1000 | 5 | 0 | >1000 |
| F 1657 | 1000 | 5 | 0 | >1000 |
| F 1659 | 1000 | 5 | 0 | >1000 |
| F 1660 | 1000 | 5 | 0 | >1000 |
| F 1683 | 1000 | 5 | 0 | >1000 |
| F 1684 | 1000 | 5 | 0 | >1000 |
| F 1685 | 1000 | 5 | 0 | >1000 |
| F 1686 | 1000 | 10 | 0 | >1000 |
| F 1687 | 1000 | 5 | 0 | >1000 |
| Levamisole | 75 | 5 | 0 | 185 |
| | 100 | 5 | 2 | |
| | 200 | 10 | 5 | |
| | 500 | 10 | 8 | |

Taking into account the pharmacological properties of these chemical compounds, they can be used in therapeutic treatments which require the use of immunomodulators, for instance in the treatment of rheumatoid polyarthritis or other ailments which may result from depressed immunity and/or wherein an elevation or restoration of the immunity response is of significance and desirable.

In tests of the same nature and comparable to those set forth in the foregoing, additional compounds of the present invention exhibit the immunomodulating activity and favorable toxicity in the same manner as those just reported.

The high order of immunomodulating activity of the active agents of the present invention, together with their favorable toxicity, is evidenced by tests in lower animals, representative of which are reported herein. These new compounds of the invention can be administered per os, e.g., in the form of pills or tablets, in which they are present together with the usual pharmaceutical carriers, excipients, binders, and the like. Tablets may be prepared conventionally by compounding one of the new compounds together with a customary carrier or adjuvant, such as talc, magnesium stearate, starch, lactose, gelatin any of numerous gums, and the like. Thus, in their most advantageous form, the compositions of the invention will contain a non-toxic pharmaceutical carrier in addition to the active immunomodulating ingredient of the present invention. Exemplary solid carriers are lactose, magnesium stearate, calcium stearate, starch, terra alba, dicalcium phosphate, sucrose, talc, stearic acid, gelatin, agar, pectin, acacia, or the like. Representative liquid carriers are peanut oil, sesame oil, olive oil, water, or the like. The active agents of the invention can be conveniently administered in such compositions containing about 0.01 to about 67 percent, preferably 0.04 to 12.15 percent, by weight of active ingredient. Such formulations are representatively illustrated in U.S. Pat. No. 3,402,244, inter alia. Thus, a wide variety of pharmaceutical forms suitable for many modes of administration and dosages may be employed. For oral administration, the active ingredient and pharmaceutical carrier may, for example, take the form of a granule, pill, tablet, losenge, elixir, syrup, or other liquid suspension or emulsion whereas, for parenteral administration, the composition may be in the form of a sterile solution and for rectal administration in the form of a suppository. For topical administration, the usual liquid suspension or emulsion, powders, creams, salves, and especially such compositions of the nature of an ointment, may be employed, with the ointment compositions being preferred.

The method of using the compounds of the present invention comprises internally or externally administering a compound of the invention, preferably admixed with the pharmaceutical carrier, for example, in the form of any of the above-mentioned compositions, or filled into a capsule, to elevate or restore a depressed immunity response in a living animal body. Illustratively, they may be employed in an amount of about 0.1 to 200 milligrams per unit dose, preferably about 2.5 to 50 milligrams for an oral dose, usually 0,1 to 25 milligrams, while parenteral dosages are usually less and ordinarily about one-half (½) of the oral dose so that the preferred parenteral unit dosage will be about 1 to about 25 milligrams. The unit dose is preferably given a suitable number of times daily so that the daily dose may vary from about 0.3 to 600 milligrams, with preferred daily dosages varying from about 7.5 to about 150 milligrams (oral) to about 3 to 75 milligrams (parenteral). For many purposes, a suitable clinical dose may be between 0.1 and 25 mg. Naturally, the dosage must be adjusted in accord with the condition, age, and weight of the patient, and it goes without saying that the immunomodulating activity of the compounds of the invention, together with their favorable toxicity, also makes them suitable for veterinary applications. The compounds are obviously subject to wide variations in optimum daily and unit dosages, due to patient body weight, conditions, and ancillary factors, and the invention therefore should not be limited by the exact ranges stated. The exact dosage, both unit dosage and daily dosage, will of course have to be determined according to established medical and/or veterinary principles. In addition, the active ingredients of the present invention or compositions containing the same may either be administered concurrently with or include other physiologically active materials and/or medicaments, such as buffering agents, antacids, sedatives, stimulants, anticholinergics, analgesics, neuroleptics, minor tranquilizers, or the like. For purposes of the method-of-treating aspects of the present invention, it is of course only necessary that an effective immunomodulating dose of a compound of the present invention be administered to the living animal body or host suffering from a depressed immunity and hence in need of such immunomodulating therapy, whether this be by the oral route or parenteral route.

A suitable tablet formulation may be as set forth in U.S. Pat. No. 4,021,564 and, of course, as previously stated, the immunomodulating compounds provided by the present invention may also be administered successfully by embodying an effective immunomodulating quantity thereof in an injectible emulsion or a suspension for injection, in oral powders, suspensions, or syrups, or in other acceptable dosage forms, such as solutions in propylene glycol.

Although as previously stated very small quantities of the active materials of the present invention are effective when minor thereapy is involved or in cases of administration to subjects having a relatively low body weight, unit dosages are usually within the range set forth above, or even higher, depending of course upon the emergency of the situation and the particular results desired. To repeat, the exact individual dosages as well as daily dosages in a particular case will of course be determined according to established medical principles under the supervision of the physician or veterinarian involved in treatment of the particular depressed immune response syndrome which is being treated.

While the invention has been described in detail and with reference to specific embodiments thereof, it will be apparent to one skilled in the art that various changes and modifications can be made therein without departing from the spirit and scope thereof.

What we claim is:

1. 4-phenyl-2-amino thiazoles having the formula:

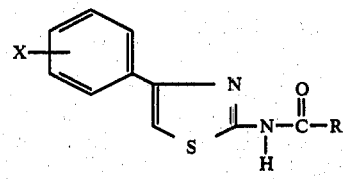

in which:
X represents a hydrogen atom, a halogen, a lower alkyl, or an alkoxy,
R represents —O—C—(Cl)$_3$; —O—CH$_2$—C(Cl)$_3$; —O—CH$_2$—CH$_2$—CH$_2$—Br; —O—CH$_2$—CHBr$_2$;
or carboxyalkyl.

2. A compound of claim 1, selected from:
4-phenyl 2-(2'-2'-2'-trichlorethoxy carboxamido) thiazole,
4-parachlorophenyl 2-(2'-2'-2'-trichlorethoxy carboxamido) thiazole,
4-paramethyl phenyl 2-(2'-2'-2'-trichlorethoxy carboxamido) thiazole, and
4-paramethoxy phenyl 2-(2'-2'-2'-trichlorethoxy carboxamido) thiazole.

3. A pharmaceutical composition, useful in immunotherapy, containing an effective immune response elevating amount of a compound of claim 1, together with a pharmaceutically acceptable carrier.

4. The pharmaceutical composition as claimed in claim 3, wherein said compound is a compound of claim 2.

5. A method for the treatment of a patient suffering from a depressed immune response condition, comprising the step of administering to said patient a compound of claim 1 in an amount effective for alleviation of said condition.

6. The method of claim 5, wherein the compound administered is a compound of claim 2.

7. The method of claim 6, wherein the compound is administered in an immune-response elevating amount.

8. Compound of claim 1 wherein R is a higher alkyl group of 8-28 carbon atoms.

9. The method of claim 5, wherein the condition treated is rheumatoid arthritis.

10. The method of claim 9, wherein the compound administered is a compound of claim 2 in an amount effective for alleviation of said condition.

11. A compound of claim 1 which is 4-phenyl 2-(2'-2'-2'-trichlorethoxy carboxamido) thiazole.

12. A pharmaceutical composition of claim 3, wherein the compound is 4-phenyl 2-(2'-2'-2'-trichlorethoxy carboxamido) thiazole.

13. The method of claim 5, wherein the compound is 4-phenyl 2-(2'-2'-2'-trichlorethoxy carboxamido) thiazole.

* * * * *

UNITED STATES PATENT AND TRADEMARK OFFICE
CERTIFICATE OF CORRECTION

PATENT NO. : 4,225,610

DATED : September 30, 1980

INVENTOR(S) : Jean-Pierre Tarayre, Henri Cousse, Gilbert Mouzin, Henri Lauressergues and Silvano Casadio It is certified that error appears in the above-identified patent and that said Letters Patent are hereby corrected as shown below:

Col. 1, lines 27 & 28; "O-CH$_2$-CH$_2$-Br," should read -- O-CH$_2$-CH$_2$-Br, --
Col. 2, line 44; "Epirical" should read -- Empirical --
Col. 3, line 43; "chromarography:" should read -- chromatography: --
Col. 4, line 35; "chromatograhy:" should read -- chromatography: --
Col. 4, line 60; "Empiricial" should read -- Empirical --
Col. 5, line 56; "20% in" should read -- 20% soluble in --
Col. 10, line 9; "80 TM" should read -- 80 (TM) --
Col. 10, Table 1, first column heading, line 5; "challange" should read -- challenge --

Col. 10, Table 1, third column, line 2; "1,8" should read -- 6,5 --
Col. 10, Table 1, third column, line 7; "P<0,05" should read -- P>0,05 --
Col. 10, Table 1, first column, lines 2 & 3; "F 1686" should be moved over to column 2 to read -- F 1686
　　　　5 mg/kg
　　　　(x 3) --
Col. 10, Table 1, third column, line 14; "(3,20)" should read -- (3,18) --
Col. 10, bottom of Table 1; "perenthesis" should read -- parenthesis --

UNITED STATES PATENT AND TRADEMARK OFFICE
CERTIFICATE OF CORRECTION

PATENT NO. : 4,225,610

DATED : September 30, 1980

INVENTOR(S) : Jean-Pierre Tarayre, Henri Cousse, Gilbert Mouzin, Henri Lauressergues and Silvano Casadio It is certified that error appears in the above-identified patent and that said Letters Patent are hereby corrected as shown below:

Col. 11, line 15; "TABLE" should read -- TABLE 3 --
Col. 14, line 14; "-O-$CH_2$-$CH_2$-$CH_2$-Br;" should read -- -O-$CH_2$-$CH_2$-Br; --
Col. 14, lines 14 & 15; "-O-$CH_2$-$CHBr_2$;" should read -- -O-$CH_2$-$CHBr_2$; --

Signed and Sealed this

Twenty-fourth Day of February 1981

[SEAL]

Attest:

RENE D. TEGTMEYER

Attesting Officer

Acting Commissioner of Patents and Trademarks

UNITED STATES PATENT AND TRADEMARK OFFICE
CERTIFICATE OF CORRECTION

PATENT NO. : 4,225,610

DATED : September 30, 1980

INVENTOR(S) : Jean-Pierre Tarayre, Henri Cousse, Gilbert Mouzin, Henri Lauressergues and Silvano Casadio It is certified that error appears in the above-identified patent and that said Letters Patent are hereby corrected as shown below:

Col. 10, Table 1, second column, lines 2 & 3; "DMSC 1 mg/kg" should read — DMSO 1 ml/kg —

Signed and Sealed this

Twelfth Day of May 1981

[SEAL]

Attest:

RENE D. TEGTMEYER

Attesting Officer

Acting Commissioner of Patents and Trademarks